United States Patent [19]

Szántay et al.

[11] 4,102,886
[45] Jul. 25, 1978

[54] PROCESS FOR THE PREPARATION OF BENZO(a)QUINOLIZIDINE DERIVATIVES

[75] Inventors: Csaba Szántay; Lajos Szabó; László Töke; Istvan Toth; Sandor Virág; Erzsébet Kanyó; Ágoston Dávid, all of Budapest, Hungary

[73] Assignee: Chinoin Gyogyszer es Vegyeszeti Termekek Gyara Rt., Budapest, Hungary

[21] Appl. No.: 624,470

[22] Filed: Oct. 21, 1975

[30] Foreign Application Priority Data

Oct. 23, 1974 [HU] Hungary .................. CI 1514
Sep. 11, 1975 [HU] Hungary .................. CI 1603

[51] Int. Cl.$^2$ ............................ C07D 455/06
[52] U.S. Cl. .................. 260/287 CF; 260/283 SY; 260/283 CN; 260/289 C; 544/126; 424/258
[58] Field of Search ............... 260/287 CF, 283 SY, 260/289 CF, 283 CN; 544/126

[56] References Cited

U.S. PATENT DOCUMENTS

| 2,830,993 | 4/1958 | Brossi et al. ............ 260/287 CF |
| 2,843,591 | 7/1958 | Brossi et al. ............ 260/287 CF |
| 3,095,419 | 6/1963 | Tretter .................... 260/287 CF |
| 3,123,609 | 3/1964 | Openshaw et al. ........ 260/287 CF |
| 3,634,431 | 1/1972 | Van Dyke ................ 260/287 CF |
| 3,635,986 | 1/1972 | Van Dyke ................ 260/287 CF |

OTHER PUBLICATIONS

House, Modern Synthetic Reactions, (1965) p. 198.
Stork et al., J.A.C.S., (1963) pp. 212–215.
March, Advanced Organic Chem., (1968) pp. 464–465.
March, "Advanced Organic Chemistry," 1968, pp. 336, I, and 865, 866, II.

*Primary Examiner*—Donald G. Daus
*Assistant Examiner*—David E. Wheeler
*Attorney, Agent, or Firm*—Karl F. Ross

[57] ABSTRACT

A process for the preparation of a compound of the formula I or a salt thereof

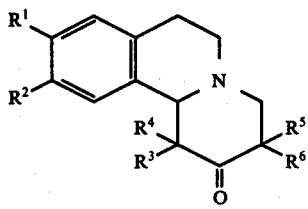

wherein
  $R^1$ and $R^2$ each represent hydrogen or a $C_{1-4}$ alkoxy group, or together form a methylenedioxy group;
  $R^3$, $R^4$, $R^5$ and $R^6$ are the same or different and are hydrogen or a group of the formula $-CH_2-(CH_2)_n-R^7$ with the proviso that at least one of the members $R^3$, $R^4$, $R^5$ and $R^6$ is other than hydrogen; $R^7$ is carboxyl or a carboxylic acid derivative group;
  n = 0.1 or 2 which comprises reacting a compound of the formula II

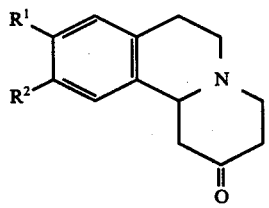

with an organic secondary amine and reacting the N-amine of the formula III

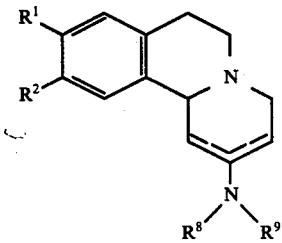

thus obtained wherein $R^8$ and $R^9$ each represent a $C_{1-5}$ alkyl group, or together with the adjacent nitrogen atom form a 5- or 6-membered heterocyclic ring which can contain a further heteroatom, with a compound of the formula IV $$CH_2=CH-(CH_2)_n-R^{10} \quad\quad (IV)$$

wherein $R^{10}$ is a cyano or alkoxycarbonyl group.

3 Claims, No Drawings

PROCESS FOR THE PREPARATION OF BENZO(a)QUINOLIZIDINE DERIVATIVES

This invention relates to quinalizidine, a process for the preparation and pharmaceutical compositions comprising the same.

According to the present invention there are provided benzo(a)quinalizidine derivatives of the formula I (I)

and salts thereof having antiinflammatory effect (wherein $R^1$ and $R^2$ each is hydrogen or a $C_{1-4}$ alkoxy group, or together form a methylenedioxy group;

$R^3$, $R^4$, $R^5$ and $R^6$ may be the same or different and are hydrogen or a group of the formula $-CH_2-(CH_2)_n-R^7$ with the proviso that at least one of the members $R^3$, $R^4$, $R^5$ and $R^6$ is other than hydrogen;

$R^7$ is a carboxyl group or a carboxylic acid derivative group;

n = 0,1 or 2).

In Hungarian Pat. Nos. 153 695 and 155 959 compounds of the formula I are disclosed, wherein $R^1$ and $R^2$ are hydrogen or alkoxy, $R^3$, $R^4$ and $R^5$ are hydrogen, $R^6$ is a group of the formula $-CH_2-(CH_2)_n-R^7$ and $R^7$ is cyano- or alkoxycarbonyl and n=1. According to these patents the above compounds are prepared by reacting 3,4-dihydroisoquinoline with quaternary salts or unsaturated ketones. Thus compounds of the above type are described in which $R^1$ and $R^2$ are methoxy.

According to the process of the present invention the compounds of the formula I (I)

and salts thereof are prepared by (a) reacting a compound of the formula II (II)

(wherein $R^1$ and $R^2$ are as stated above) with an organic secondary amine and reacting the amine of the formula III (III)

thus obtained (wherein $R^1$ and $R^2$ are as stated above, and $R^8$ and $R^9$ each represent a $C_{1-5}$ alkyl group, or together with the adjacent nitrogen atom form a 5- or 6-membered heterocyclic ring, which may optionally contain a further heteroatom) with a compound of the formula IV $$CH_2 = CH - (CH_2)_n - R^{10} \quad (IV)$$

(wherein $R^{10}$ stands for a cyano or alkoxycarbonyl group and n is as stated above); or (b) for the preparation of compounds of the formula V (V)

(wherein $R^1$, $R^2$ and $R^7$ are as stated above and n=0 or (1) reacting a compound of the formula VI (VI)

(wherein $R^1$ and $R^2$ are as stated above) with a compound of the formula VII $$CH_3-\underset{\underset{O}{\|}}{C}-\underset{\underset{CH_2-N(CH_3)_2}{|}}{CH}-CH_2-(CH_2)_n-R^{10} \quad (VII)$$

(wherein $R^{10}$ is as stated above and n=0 or 1) and, if desired converting in a compound thus obtained the $R^{10}$ group into an $R^7$ group by hydrolysis, ammonolysis, halogenating and/or esterification, and, if desired, converting a compound of the formula I into a salt thereof.

According to a preferred embodiment of method (a) the enamines of the formula III are prepared by reacting a compound of the formula II with morpholine, piperidine, pyrrolidine or a dialkylamine, particularly diethylamine.

The enamines of the formula III thus obtained are then preferably reacted with acryl nitrile or an alkylacrylate, particularly diethyl-acrylate.

The term "carboxylic acid derivative group" encompasses all usual carboxylic acid derivative groups, e.g. alkoxycarbonyl (e.g. methoxycarbonyl, etc.), phenoxycarbonyl, phenylalkoxycarbonyl, carbonyl halide (e.g. carbonylchloride), carbamoyl or substituted carbamoyl groups. The carbamoyl group may be substituted by alkyl (e.g. methyl, ethyl, etc.), aryl (e.g. phenyl) groups. The carboxylic acid derivative group may be a N-heterocyclic carbonyl group (e.g. morpholinocarbonyl group) or an aralkylcarbamoyl group (e.g. benzylaminocarbonyl group).

The terms "alkyl group" and "alkoxy group" used throughout the specification relate to straight or branched chain groups having 1-7, preferably 1-4 carbon atoms (e.g. methyl, methoxy, ethyl, ethoxy, n-propyl, isopropoxy, etc.).

The position and number of the groups of the formula $-CH_2-(CH_2)_n-R^7$ introduced into the compounds of the formula III varies strongly from the reaction conditions and can be influenced by modifying the said conditions. An excess of the starting material of the formula IV enhances the formation of multisubstituted derivatives. By using polar protic solvents (e.g. ethanol, methanol) 3-monosubstituted derivatives while, on using apolar solvents (e.g. benzene, toluene), 1-monosubstituted derivatives are obtained. If the reaction is carried out in a polar protic solvent at elevated temperature, the formation of disubstituted derivatives is observed.

In a compound thus obtained the alkoxycarbonyl or nitrile group may be converted into other groups, i.e. a group $R^{10}$ may be converted into a group $R^7$. Thus an alkoxycarbonyl or nitrile group may be converted into a carboxyl, halogenocarbonyl, or optionally substituted carbamoyl (alkyl-, aryl or aralkylsubstituted carbamoyl) or N-heterocyclic carbonyl (e.g. morpholinocarbonyl) group.

These subsequent reactions may be carried out by methods known per se. Thus an alkoxycarbonyl group may be converted into a carboxyl group by hydrolysis or reacted with the corresponding amines. The acid amides may be also prepared by reacting a free carboxylic acid with a halogenating agent (e.g. thionylchloride) and reacting the acid halide thus obtained with the corresponding amine.

The compounds of the formula I may be transformed into their salts. The said salts may be formed by inorganic acid (e.g. hydrochloric acid, hydrobromic acid, etc.) or organic acids (e.g. acetic acid, citric acid, etc.). Salt formation may also be carried out by methods known per se. One may proceed preferably by reacting a compound of the formula I with the solution of the corresponding acid formed with alcohol.

According to a further aspect of the present invention, there are provided pharmaceutical compositions having antiinflammatory effect comprising as active ingredient a compound of the formula I or a salt thereof

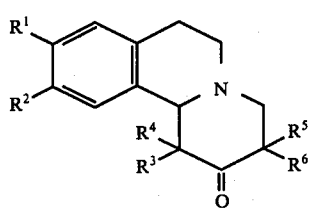

(wherein
$R^1$ and $R^2$ each are hydrogen or $C_{1-4}$ alkoxy or together form a methylenedioxy group;
$R^3$, $R^4$, $R^5$ and $R^6$ are hydrogen or a group of the formula $-CH_2-(CH_2)_n-R^7$ with the proviso that at least one of the members $R^3$, $R^4$, $R^5$ and $R^6$ is other, than hydrogen;
$R^7$ is a carboxylic group of a carboxylic acid derivative group;
$n = 0.1$ or 2, with the further proviso that if $R^3$, $R^4$ and $R^5$ are hydrogen and $R^7$ in the $R^6$ is cyano or alkoxycarbonyl and n =1, than $R^1$ and $R^2$ are hydrogen, $C_{2-4}$ alkoxy, or together form a methylenedioxy group) in admixture with suitable inert solid or liquid carriers.

The pharmaceutical compositions of the present invention may be prepared by methods of the pharmaceutical industry known per se. The compositions may be put up in solid (e.g. tablets, pills, coated pills, etc.) and liquid (e.g. solution, emulsion and suspension) form. The composition may be suitable for oral, parenteral and rectal administration. The inert diluents may be starch, calcium-carbonate, magnesiumstearate, magnesium-carbonate, water, polyalkyleneglycol, etc.

The dosage of the active ingredient may vary within a wide range and depends on the requirements of the given case. Generally it may be stated that the daily dosage of the active ingredient of the formula I may be from about 300 mg to about 500 mg. It is preferred to use the compositions in the dosage unit formed of tablets or capsules comprising from about 50 mg to about 150 mg of a compound of the formula I.

The benzo(a)quinolizidine derivatives of the formula (I) possess valuable pharmacological effects, and can be used primarily as potent antiphlogistic agents. In the following there are summarized the pharmacological tests performed with the compounds of the formula (I), and the results of these tests. The compounds examined in the pharmacological tests were represented by the following symbols: (see formula V)

| Symbol | $R^1$ | $R^2$ | $R^7$ | n |
|---|---|---|---|---|
| SC 118 | —O—H$_2$—O— | | CN | 1 |
| SCT-1 | —OCH$_3$ | —OCH$_3$ | CN | 1 |
| SCT-2 | —OCH$_3$ | —OCH$_3$ | CH$_3$COO— | 1 |
| SCT-3 | —OC$_2$H$_5$ | —OC$_2$H$_5$ | CN | 1 |

As evidenced by the results of the different tests, the benzo(a)quinolizidine derivatives of the formula (I) possess the same or even more potent antiphlogistic effect than phenylbutazone.

Inhibition of Kaolin- and carrageenin-induced oedema

The tests were carried out on groups each consisting of at least 10 animals. The percentage inhibition of oedema, in relation to the untreated controls, was determined for each of the animals, and the average values were calculated. These average values are listed in Table 1 below.

Table 1

| Compound | Dosage mg./kg. p.o. | Inhibition of kaolin-induced oedema 2 hours after administration, % | Inhibition of carrageenin-induced oedema 1.5 hours after administration, % |
|---|---|---|---|
| SC 118 | 25 | 18.1+ | 22.0+ |
| | 50 | 27.5+ | 30.6++ |
| | 75 | 43.7++ | 47.7++ |
| | 100 | 53.4++ | 52.7++ |
| SCT-1 | 25 | 20.5+ | — |
| | 50 | 21.4+ | 24.2+ |
| | 75 | 24.8+ | 25.7+ |
| | 100 | 47.8++ | 37.7++ |
| SCT-2 | 25 | 5.8 | — |
| | 50 | 21.4+ | 14.3 |
| | 75 | 24.7+ | 2.8 |
| | 100 | — | 17.0 |

Table 1-continued

| Compound | Dosage mg./kg. p.o. | Inhibition of kaolin-induced oedema 2 hours after administration, % | Inhibition of carrageenin-induced oedema 1.5 hours after administration, % |
|---|---|---|---|
| SCT-3 | 25 | 17.3+ | 25.1+ |
|  | 50 | 19.4+ | 41.5++ |
|  | 75 | 48.9++ | — |
|  | 100 | 45.9++ | 53.7++ |
| Phenylbutazone | 50 | 27.5++ | 24.3+ |
| Indomethacine | 10 | 27.2++ | 26.7+ |
| Na-salicylate | 100 | 10.5 | 16.2 |

$^+p = 0.01$
$^{++}p = 0.05$ (significance levels according to Student's "t" probe)

Cotton granuloma test

Table 2

| Compound | Dosage (mg./kg.) | Effect,% | p |
|---|---|---|---|
| SC-118 | 50 | 26.4 | 0.01 |
| Phenylbutazone | 50 | 19.6 | 0.05 |
| Na-salicylate | 100 | 25.5 | 0.05 |

The benzo(a)quinolisidine derivatives according to the invention exert outstandingly high activities in the inhibition of serotonine-induced oedema, superseding many times the activities of phenylbutazone and indomethacine.

Tests performed on serotonine-induced oedema

The tests were carried out on groups each consisting of 10 animals. The percentage inhibition of oedema, in relation to the untreated controls, was determined for each of the animals. The data listed in Table 3 are the averages of the inhibition values.

Table 3

| Compound | Dosage (mg./kg.) p.o. | Percentage inhibition 1 hour after administration |
|---|---|---|
| SC-118 | 25 | 28.5+ |
|  | 50 | 42.1+ |
|  | 75 | 48.7+ |
| SCT-1 | 50 | 22.4+ |
|  | 100 | 57.8+ |
| SCT-2 | 100 | 16.0 |
| SCT-3 | 50 | 36.2+ |
|  | 100 | 47.0+ |
| Phenylbutazone | 100 | 10.2 |
| Indomethacine | 25 | 1.4 |

$^+p = 0.001$ (Student's "t" probe).

Besides their antiphlogistic activities, some of the benzo(a)quinolizidine derivatives exert antipyretic effects as well. On the basis of the tests performed on experimentally provoked fever, the antipyretic activities of the compounds according to the invention surpass the effect of amidazophenum.

Antipyretic activity

Table 4

| Compound | Dosage mg./kg. p.o. | Variation of body temperature 1  2  3 hours after administration | | |
|---|---|---|---|---|
| SC-118 | 50 | −2.75+++ | −3.34+++ | −4.03+++ |
|  | 25 | −1.67+++ | −1.81+++ | −1.60++ |
| Phenylbutazone | 50 | −1.05++ | −1.07++ | −0.76+ |
|  | 25 | −0.82++ | −0.84++ | −0.73+ |
| Amidazophenum | 25 | −1.17+++ | −0.94++ | −0.95++ |

$^+p = 0.05$
$^{++}p = 0.01$
$^{+++}p = 0.001$

Furthermore, as evidenced by the results of the hot-plate and writhing tests, the compounds according to the invention possess analgesic effects as well. In this respect the compounds according to the invention are superior to phenylbutazone.

Examination of the analgesic effect by the hot-plate test

Table 5

| Compound | Dosage mg./kg. p.o. | Prolongation of the reaction time, % (2 hours after administration) |
|---|---|---|
| SC-118 | 50 | 61.2 |
| SCT-2 | 50 | 26.4 |
| SCT-3 | 50 | 33.9 |
| Indomethacine | 50 | no evaluable effect can be observed |
| Phenylbutazone | 50 |  |

Examination of the analgesic effect by the writhing test

Table 6

| Compound | Dosage mg./kg. p.o. | Activity, % (reduction of the number of writhings in relation to the controls) |
|---|---|---|
| SC-118 | 50 | 41.8 |
| Phenylbutazone | 100 | 17.6 |

Besides the antiphlogistic and antipyretic effects, the new benzo(a)quinolizidine derivatives also exercise a sedative effect on the central nervous system.

Narcosis potentiating effect

Table 7

| Compound | Dosage mg./kg. p.o. | Prolongation of the sleep period in relation to the untreated controls, % |
|---|---|---|
| SC-118 | 50 | 253.0 |
|  | 25 | 96.4 |
| SCT-1 | 50 | 207.6 |
|  | 25 | 132.8 |
| SCT-2 | 50 | 28.3 |
| SCT-3 | 50 | 240.2 |
|  | 25 | 131.7 |
| Meprobamate | 20 | 110.2 |

The results of the toxicity examinations indicate that most of the benzo(a)quinolizidine compounds according to the invention have about the same degree of toxicity as phenylbutazone.

Acute toxicity tests

The acute toxicity values of the compounds were determined on rats, after oral administration. The LD$_{50}$ values were calculated according to the Litchfield-Wildoxon method. The results are summarized in Table 8.

Table 8

| Compound | LD$_{50}$ mg./kg. p.o. |
|---|---|
| SC-118 | 1407.63 |
| SCT-1 | 620 |
| SCT-3 | 780 |
| Aspirin | 1700 |

Table 8-continued

| Compound | LD$_{50}$ mg./kg. p.o. |
|---|---|
| Phenylbutazone | 1181.45 |
| Indomethacine | 12 |

In order to give a more detailed information, in the following there are given the results of the toxicity tests performed with compound SC-118. The tests were carried out on CFY rats, each weighing 150 to 200 g.

Table 9

| Dosage mg./kg. | Dead animals/treated animals | | | | | |
|---|---|---|---|---|---|---|
| | 24 hours | | 48 hours after administration | | 72 hours | |
| | m | f | m | f | m | f |
| 750 | 0/10 | 0/10 | 0/10 | 0/10 | 0/10 | 0/10 |
| 1000 | 1/10 | 2/10 | 2/10 | 2/10 | 2/10 | 2/10 |
| 1250 | 2/10 | 3/10 | 3/10 | 3/10 | 3/10 | 3/10 |
| 1500 | 5/10 | 6/10 | 5/10 | 6/10 | 5/10 | 6/10 |
| 1750 | 6/10 | 6/10 | 8/10 | 8/10 | 8/10 | 8/10 |
| 2000 | 10/10 | 10/10 | 10/10 | 10/10 | 10/10 | 10/10 |

LD$_{50}$, m = 1425 mg./kg.
LD$_{50}$, f = 1400 mg./kg.
m = male
f = female

When examining the subtoxic effects it appeared that none of the compounds according to the invention exert ulcerogeneous effects or harmful influence on the haematopoietic system, either. As a comparison it should be noted e.g. indomethacine has a marked ulcerogeneous effect.

Determination of ulcer index

Table 10

| Compound | Ulcer | | Erosion | |
|---|---|---|---|---|
| | male | female | male | female |
| SC-118 | 0/10 | 0/10 | 0/10 | 0/10 |
| SCT-1 | 1/10 | 2/10 | 3/10 | 4/10 |
| SCT-3 | 1/10 | 0/10 | 6/10 | 4/10 |
| Control | 0/10 | 0/10 | 0/10 | 0/10 |
| Indomethacine | 3/10 | 3/10 | 1/10 | 1/10 |
| Phenylbutazone | 3/10 | 1/10 | 0/10 | 0/10 |
| Na-salicylate | 4/10 | 2/10 | 1/10 | 3/10 |

Thus the benzo(a)quinolizidine derivatives of the formula (I) are substances with significant antiphlogistic effects, possessing valuable antipyretic and analgesic activities as well. The sedative effects of these compounds are also not negligible. Moreover, these compounds are completely devoid of the undesired side-effects (e.g. ulcerogeneous effect) characteristic of the nonsteroidal antiphlogistic agents, and their therapeutical indices are far more favorable than that of indomethacine.

Therapeutical indices

Table 11

| Compound | Therapeutical index LD$_{50}$/ED$_{50}$ | |
|---|---|---|
| | kaolin-oedema | carrageenin-oedema |
| SC-118 | 29.2 | 22.6 |
| SCT-1 | 12.4 | 6.7 |
| SCT-3 | 15.0 | 19.8 |
| Indomethacine | 2.3 | 1.3 |

Based on the above, the compounds according to the invention can be used as antiphlogistic and analgesic agents primarily in the treatment of disorders evoked by the inflammation of joints and skeletal musculature.

Because of their non-ulcerogeneous character and of the lack of harmful side-effects on the haematopoietic system, these compounds can also be administered for a prolonged period, which is very desirable in the treatment of the above-mentioned disorders.

The invention is elucidated in detail in the following non-limiting Examples.

EXAMPLE 1

2-Oxo-3-($\beta$-methoxycarbonyl-ethyl)-9,10-methylenedioxy-1,2,3,4,6,7-hexahydro-11bH-benzo(a)quinolizidine 1.0 g. (4.98 mmoles) of 4-dimethylaminomethyl-5-oxo-capric acid methyl ester are added to a solution of 1.0 g. (4.95 mmoles) of 9,10-methylenedioxy-isoquinoline hydrochloride in 3 ml. of distilled water, and the reaction mixture is allowed to stand for one day. The separated substance is filtered off, and washed successively with water and methanol. 1.5 g. (92%) of 2-oxo-3-($\beta$-methoxycarbonylethyl)-9,10-methylenedioxy-1,2,3,4,6,7-hexahydro-11bH-benzo(a)quinolizidine are obtained; m.p. 123°–124° C (after recrystallization from methanol).

Characteristic IR-bands (in KBr): 2750, 2800 cm$^{-1}$ (Bohlmann-bands), 1750 cm$^{-1}$ (CH$_3$COO—) and 1740 cm$^{-1}$ (C=O).

NMR-spectrum (in deuterochloroform): $\tau$ = 3.38 (C$_{11}$—H), 3.42 (C$_8$—H), 4.10 (—O—CH$_2$—O—) and 6.30 (CH$_3$COO—).

EXAMPLE 2

2-Oxo-3-($\beta$-cyano-ethyl)-9,10-methylenedioxy-1,2,3,4,6,7-hexahydro-11bH-benzo(a)quinolisidine 1.0 g. (5.92 mmoles) of 4-dimethylaminomethyl-5-oxo-capronitrile are added to a solution of 1.0 g. (4.95 mmoles) of 9,10-methylenedioxy-isoquinoline hydrochloride in 3 ml. of distilled water, and the mixture is allowed to stand for one day. The separated crystalline substance is filtered off, and washed successively with water and methanol. 0.9 g. (64%) of 2-oxo-3-($\beta$-cyano-ethyl)-9,10-methyleneidoxy-1,2,3,4,6,7-hexahydro-11bH-benzo(a)quinolizidine are obtained; m.p.: 154°–155° C (after recrystallization from methanol).

Characteristic IR-bands (in KBr): 2380 cm$^{-1}$ (CN), 1715 cm$^{-1}$ (C=O), 2750, 2800 cm$^{-1}$ (Bohlmann-bands).

NMR-spectrum (in deuterochloroform): $\tau$ = 3.48 (C$_{11}$—H), 3.53 (C$_8$—H) and 4.18 (—O—CH$_2$—O—).

EXAMPLE 3

2-Oxo-3-($\beta$-methoxycarbonyl-ethyl)-9,10-dimethoxy-1,2,3,4,6,7-hexahydro-11bH-benzo(a)quinolizidine 1.0 g. of 4-dimethylaminomethyl-5-oxo-capric acid methyl ester is added to a solution of 1.0 g. (4.4 mmoles) of 9,10dimethoxyisoquinoline hydrochloride in 3 ml. of distilled water, and the reaction mixture is allowed to stand for one day. The separated crystalline substance is filtered off, and washed successively with water and methanol. 1.45 g. (95%) of 2-oxo-3-($\beta$-methoxycarbonyl-ethyl)-9,10-dimethoxy-1,2,3,4,6,7-hexahydro-11bH-benzo(a)quinolizidine are obtained; m.p.: 131° C (see also Tetrahedron Letters 26, 2975 (1966).

EXAMPLE 4

2-Oxo-3-($\beta$-cyano-ethyl)-9,10-dimethoxy-1,2,3,4,6,7-hexahydro-11bH-benzo(a)quinolizidine 1.0 g. (5.92 mmoles) of 4-dimethylaminomethyl-5-oxo-capronitrile is added to a solution of 1.0 g. (4.4 mmoles) of 9,10 dimethoxyisoquinoline hydrochloride in 3 ml. of distilled water, and the reaction mixture is allowed to stand for one day. The separated substance is filtered off, and washed first with water and then with a small amount of methanol. 0.85 g. (62%) of 2-oxo-3-(β-cyano-ethyl)-9,10-dimethoxy-1,2,3,4,6,7-hexahydro-11bH-benzo(a)quinolizidine are obtained; m.p.: 130°–131° C (see also Tetrahedron Letters 26, 2975 (1966).

EXAMPLE 5

2-Oxo-3-(β-carboxy-ethyl)-9,10-methylenedioxy-1,2,3,4,6,7-hexahydro-11bH-benzo(a)quinolizidine A mixture of 5.0 g (15.1 mmoles) of 2-oxo-2-(β-methoxycarbonyl-ethyl)-9,10-methylenedioxy-1,2,3,4,6,7-hexahydro-11bH-benzo(a)quinolizidine, 60 ml. of 10% hydrochloric acid and 40 ml. of methanol is heated on a steam bath for 3 hours. Thereafter the mixture is evaporated in vacuo to dryness, and the residue is recrystallized from a mixture of methanol and ether. 5.2 g. (98%) of 2-oxo-3-(β-carboxy-ethyl)-9,10-methylenedioxy-1,2,3,4,6,7-hexahydro-11bH-benzo(a)quinolizidine are obtained; m.p.: 196°–197° C.

Characteristic IR-bands (in KBr): 1715 cm$^{-1}$ (C=O), (COOH).

EXAMPLE 6

2-Oxo-3-(β-aminocarbonyl-ethyl)-9,10-methylenedioxy-1,2,3,4,6,7-hexahydro-11bH-benzo(a)quinolizidine A mixture of 3.0 g. (9.0 mmoles) of 2-oxo-3-(β-methoxycarbonyl-ethyl)-9,10-methylenedioxy-1,2,3,4,6,7-hexahydro-11bH-benzo(a)quinolizidine and 50 ml. of a 10% methanolic ammonia solution is heated in a sealed tube at 100° C for one day. Thereafter the mixture is evaporated to dryness, and the residue is recrystallized from methanol. 2.8 g. (98%) of 2-oxo-3-(β-aminocarbonyl-ethyl)-9,10-methylenedioxy-1,2,3,4,6,7-hexahydro-11bH-benzo(a)quinolizidine are obtained; m.p.: 196°–197° C.

Characteristic IR-bands (in KBr): 3060, 3180 cm$^{-1}$ (NH), 2750–2800 cm$^{-1}$ (Bohlmann-bands), 1660–1690 cm$^{-1}$ (C=O, CONH$_2$).

EXAMPLE 7

2-Oxo-3-(β-chlorocarbonyl-ethyl)-9,10-methylenedioxy-1,2,3,4,6,7-hexahydro-11bH-benzo(a)quinolizidine 5.0 g. (42 mmoles) of thionyl chloride are reflux condensed, to 5.0 g. (14.2 mmoles) of 2-oxo-3-(β-carboxy-ethyl)-9,10-methylenedioxy-1,2,3,4,6,7-hexahydro-11bH-benzo(a)quinolisidine. During the addition the mixture is stirred vigorously. A strong gas evolution sets in. The mixture is heated on a steam bath for one hour, thereafter it is diluted with 20 ml. of dry benzene, and the obtained mixture is evaporated to dryness in vacuo. The residue is triturated with petroleum ether, and the solids are filtered off. 5.3 g. (100%) of 2-oxo-3-(β-chlorocarbonyl-ethyl)-9,10-methylenedioxy-1,2,3,4,6,7-hexahydro-11bH-benzo(a)quinolizidine are obtained; m.p.: 110° C.

Characteristic IR-bands (in KBr): 1735, 1770 cm$^{-1}$ (C=O), (COCl).

EXAMPLE 8

2-Oxo-3-(β-benzoylaminocarbonyl-ethyl)-9,10-methylenedioxy-1,2,3,4,6,7-hexahydro-11bH-benzo(a)-quinolizidine 0.5 g. (1.34 mmoles) of the acid chloride prepared as described in Example 7 are suspended in 15 ml. of dioxane, and 0.23 g. (2.68 mmoles) of triethylamine are added to the suspension. The reaction mixture is heated to 50° C under stirring, and thereafter 0.143 g. (1.34 mmoles) of benzylamine are added. The reaction mixture is stirred at 50° C for one hour, thereafter it is cooled to room temperature, filtered, and the filtrate is evaporated to dryness in vacuo. The residue is triturated with 10 ml. of water, the liquid is decanted, and 10 ml. of dry benzene are added to the solid. The benzene is evaporated in order to remove the spures of water, and the residue is recrystallized from methanol. 0.45 g. (86%) of 2-oxo-3-(β-benzoylaminocarbonyl-ethyl)-9,10-methylenedioxy-1,2,3,4,6,7-hexahydro-11bH-benzo(a)quinolizidine are obtained; m.p.: 188°–189° C.

Characteristic IR-bands (in KBr): 3230 cm$^{-1}$ (NH), 1695 cm$^{-1}$ (C=O), 1635 cm$^{-1}$ (CONH-).

NMR-spectrum (in deuterochloroform): τ = 3.50, 3.56 (aromatic protons), 4.20 (—O—CH$_2$—O—), 5.63, 5.73 (CH$_2$).

EXAMPLE 9

2-Oxo-3-(β-morpholinocarbonyl-ethyl)-9,10-methylenedioxy-1,2,3,4,6,7-hexahydro-11bH-benzo(a)-quinolizidine 0.5 g. (1.34 mmoles) of the acid chloride prepared as described in Example 7 are suspended in a mixture of 3 ml. of absolute chloroform and 10 ml. of dioxane, and 0.35 g. (4.02 mmoles) of morpholine are added to the suspension. The reaction mixture is allowed to stand for one day, and then the solution is extracted with 30 ml. of dichloromethane. The extract is dried, and evaporated to dryness. The residue is recrystallized from methanol. 0.35 g. (67.5%) of 2-oxo-3-(β-morpholinocarbonyl-ethyl)-9,10-methylenedioxy-1,2,3,4,6,7-hexahydro-11bH-benzo(a)quinolizidine are obtained; m.p.: 168.5° C.

Characteristic IR-bands (in KBr): 2750, 2800 cm$^{-1}$ (Bohlmann-bands), 1700 cm$^{-1}$ (C=O), 1640 cm$^{-1}$ (CONH).

NMR-spectrum (in deuterochloroform): τ = 3.50, 3.56 (aromatic protons), 4.20 (—O—CH$_2$—O—), 6.49 (morpholine-protons).

EXAMPLE 10

2-Oxo-3-(β-diethylaminocarbonyl-ethyl)-9,10-methylenedioxy-1,2,3,4,6,7-hexahydro-11bH-benzo(a)-quinolizidine 0.5 g. (1.34 mmoles) of the acid chloride prepared as described in Example 7 are suspended in a mixture of 3 ml. of chloroform and 10 ml. of dioxane, and 0.129 g. (4.08 mmoles) of diethylamine are added to the suspension. The reaction mixture is stirred at room temperature for one day. Thereafter the mixture is diluted with 30 ml. of water, and extracted with 30 ml. of chloroform. The chloroform phase is dried and evaporated to dryness. The residue is purified by preparative layer chromatography, converted into its hydrochloride, and the hydrochloride is crystallized from a mixture of methanol and ether. 0.25 g. (46.5%) of 2-oxo-(β-diethylaminocarbonyl-ethyl)-9,10-methylenedioxy- 1,2,3,4,6,7-hexahydro-11bH-benzo(a)quinolizidine hydrochloride are obtained; m.p.: 175°–176° C.

Characteristic IR-bands (in KBr): 1730 cm$^{-1}$ (C=O), 1630 cm$^{-1}$ (CON).

EXAMPLE 11

2-Oxo-3-($\beta$-methyoxycarbonyl-ethyl)-9,10-diethoxy-1,2,3,4,6,7-hexahydro-11bH-benzo(a)quinolizidine 1.0 g. (3.95 mmoles) of 9,10-diethoxyquinoline hydrochloride is dissolved in 3 ml. of distilled water, and 0.8 g. (3.98 mmoles) of 4-dimethylaminomethyl-5-oxocapric acid methyl ester are added to the solution. The mixture is allowed to stand for one day. The separated crystals are filtered off, and washed successively with water and methanol. 1.4 g. (94.5%) of 2-oxo-3-($\beta$-methoxycarbonylethyl)-9,10-diethoxy-1,2,3,4,6,7-hexahydro-11bH-benzo(a)-quinolizidine are obtained; m.p.: 130°–132° C (after recrystallization from methanol).

Characteristic IR-bands (in KBr): 2750, 2800 cm$^{-1}$ (Bohlmann-bands), 1730 cm$^{-1}$ (CH$_3$COO—), 1715 cm$^{-1}$ (C=O).

EXAMPLE 12

2-Oxo-3-($\beta$-cyano-ethyl)-9,10-diethoxy-1,2,3,4,6,7-hexahydro-11bH-benzo(a)quinolizidine 1.0 g. (3.95 mmoles) of 9,10-diethoxyquinoline hydrochloride is dissolved in 3 ml. of distilled water, and 0.8 g. (4.75 mmoles) of 4-dimethylaminomethyl-5-oxocapronitrile are added to the solution. The reaction mixture is allowed to stand for one day, thereafter the separated crystals are filtered off, and washed successively with water and methanol. 1.2 g. (89%) of 2-oxo-3-($\beta$-cyanoethyl)-9,10-diethoxy-1,2,3,4,6,7-hexahydro-11bH-benzo(a)-quinolisidine are obtained; m.p.: 135°–136° C (after recrystallization from methanol).

Characteristic IR-bands (in KBr): 2750, 2800 cm$^{-1}$ (Bohlmann-bands), 2300 cm$^{-1}$ (CN), 1710 cm$^{-1}$ (CO).

EXAMPLE 13

2-Oxo-3-($\beta$-cyano-ethyl)-9,10-dimethoxy-1,2,3,4,6,7-hexahydro-11bH-benzo(a)quinolizidine A mixture of 1.2 g. (3.82 mmoles) of 1,2,3,4,6,7-hexahydro-9,10-dimethoxy-2,3-dehydro-2-pyrrolidino-11bH-benzo(a)quinolizidine, 10 ml of anhydrous ethanol and 0.346 g. (1.7-fold amount) of acrylnitrile is heated to boiling for 8 hours, whereupon the reaction mixture is cooled and evaporated. The residue is shaken with a 2.5% sodium bicarbonate solution and extracted five times with 10 ml. of ether each. The ether extract is dried, evaporated to dryness and the residue is crystallized from methanol. Thus 2-oxo-3-($\beta$-cyano-ethyl)-1,2,3,4,6,7-hexahydro-9,10-dimethoxy-11bH-benzo(a)-quinolizidine is obtained; M.p.: 131° C.

Characteristic IR bands (in KBr) 2750–2800 (Bohlmann-bands), 2270 (C | N), 1710 (C=O), 1605 cm$^{-1}$ (aromatic).

EXAMPLE 14

2-Oxo-1-($\beta$-cyano-ethyl)-9,10-dimethoxy-1,2,3,4,6,7-hexahydro-11bH-benzo(a)quinolizidine A mixture of 0.535 g. (1.7 mmoles) of 1,2,3,4,6,7-hexahydro-9,10-dimethoxy-2,3-dehydro-2-pyrrolidino-11bHbenzo(a)quinolizidine, 7 ml of anhydrous benzene and 90 mg. (1.7 mmoles) of acryl nitrile is allowed to stand for 4 days, whereupon the reaction mixture is poured into water, separated, the benzene layer is dried and evaporated to dryness. The residue is separated on a KG-PF$_{254-366}$ plate by using a benzene-methanol (14-2) mixture. Elution is carried out with acetone. The product is obtained from the upper layer. The melting point of the 2-oxo-1-($\beta$-cyanoethyl)-9,10-dimethoxy-1,2,3,4,6,7-hexahydro-9,10-dimethoxy-11bH-benzo(a)-quinolizidine amounts to 181°–182° C.

Analysis: for the formula C$_{18}$H$_{22}$N$_2$O$_3$ (314,38); calculated: C 68.76: H 7,05: N 8.91%; found: C 68.14: H 7.16: N 9.22%.

Characteristic IR bands (in KBr) 2750–2800 (Bohlmann-bands) 2280 (CN), 1715 (C=O), 1620 cm$^{-1}$ (aromatic).

EXAMPLE 15

2-Oxo-bis($\beta$-cyano-ethyl)-9,10-dimethoxy-1,2,3,4,6,7-hexahydro-11bH-benzo(a)quinolizidine A mixture of 0.9 g. (2.86 mmoles) of 1,2,3,4,6,7-hexahydro-9,10-dimethoxy-2,3-dehydro-2-pyrrolidino-11bH-benzo(a)-quinolizidine, 8 ml. of anhydrous ethanol and 0.58 ml. of acryl nitrile (3-fold amount) is heated to boiling for 4 hours. The reaction mixture is poured on 25 ml. of water, the precipitated crystals are filtered and heated to boiling with methanol. The melting point of the 2-oxo-bis-($\beta$-cyano-ethyl)-9,10-dimethoxy-1,2,3,4,6,7-hexahydro-11bH-benzo(a)quinolizidine amounts to 183°–184° C.

Analysis: for the formula C$_{21}$H$_{25}$N$_3$O$_3$ (267.44); calculated: C 48.64: H 6.86: N 11.43%; found: C 68.00: H 6.82: N 11.60%.

Characteristic IR bands (in KBr) 2750–2800 (Bohlmann-bands), 2300 (C | N), 1715 (C=O), 1610 cm$^{-1}$ (aromatic).

EXAMPLE 16

2-Oxo-3-($\beta$-methoxy-carbonyl-ethyl)-9,10-dimethoxy-1,2,3,4,6,7-hexahydro-11bH-benzo(a)quinolizidine 0.56 g. (1.78 mmoles) of 1,2,3,4,6,7-hexahydro-9,10-dimethoxy-2,3-dehydro-2-pyrrolidino-11bH-benzo(a)-quinolizidine are dissolved in 7 ml. of anhydrous benzene, whereupon 1.53 g. (1.78 mmoles) of methyl-acrylate are added and the reaction mixture is allowed to stand at room temperature for 4 days, whereupon it is poured into 50 ml. of water, the organic phase is dried, and evaporated to dryness. The residue is purified on a KG-PF$_{254-366}$ plate, as developing solvent a 14:2 mixture of benzene and methanol is used. The melting point of the 2-oxo-3-($\beta$-methoxycarbonyl-ethyl)-1,2,3,4,6,7-hexahydro-9,10-dimethoxy-11bH-benzo(a)quinolisidine amounts to 131° C.

Characteristic IR bands (in KBr) 2750–2800 (Bohlmann-bands), 1737, 1700 (COOCH$_3$, CO), 1605 cm$^{-1}$ (aromatic).

EXAMPLE 17

The enamines are prepared as follows:

Into a flask equipped with a magnetic stirrer, 1.4 g. (5.35 mmoles) of 2-oxo-1,2,3,4,6,7-hexahydro-9,10-dimethoxy-11bH-benzo(a)quinolizidine, 10.5 ml. of pyrrolidine and 22 ml. of anhydrous benzene are added. The reaction mixture is distilled off under nitrogen while stirring and anhydrous benzene containing 10% of pyrrolidine are added dropwise at at rate, which corresponds to the speed of distillation. After 5 hours the solution is evaporated to dryness. Thus amorphous 1,2,3,4,6,7-hexahydro-9,10-dimethoxy-2,3-dehydro-2-pyrrolidino-11bH-benzo(a)quinolizidine is obtained.

Characteristic IR bands (in KBr) 2750–2800 (Bohlmann-bands), 1650 (C=C, enol), 1605 cm$^{-1}$ (aromatic). The morpholino-derivative is obtained in an analogous manner.

What we claim is:

1. A process for the preparation of a compound of the formula (I)

or a salt thereof wherein

R$^1$ and R$^2$ are each hydrogen or a C$_1$ to C$_4$ alkoxy group, or together form a methylenedioxy group;
one of R$^3$, R$^4$, R$^5$ and R$^6$ is —(CH$_2$)—(CH$_2$)$_n$—R$^7$ and each remaining moiety is a hydrogen;
R$^7$ is cyano, carboxy or alkoxycarbonyl wherein the alkoxy group has 1 to 7 carbon atoms; and
n is 0,1 or 2; which comprises the steps of
(a) reacting a compound of the formula (II)

with an organic secondary amine;
(b) reacting in a predetermined solvent the resulting enamine (III)

thus obtained, wherein R$^8$ and R$^9$ each represent a C$_1$ to C$_5$ alkyl group, or together with the adjacent nitrogen atom form a 5- or 6- membered heterocyclic ring, with a compound of the formula:

$$CH_2=CH-(CH_2)_n-R^{10} \qquad (IV)$$

wherein R$^{10}$ is a cyano group, carboxy or alkoxycarbonyl wherein the alkoxy group has 1 to 7 carbon atoms; and
(c) treating the reaction mixture of step (b) with water to yield the compound of Formula I or said salt thereof, wherein the position of substitution in step (b) is determined by the use of a polar protic solvent for causing substitution at R$^5$ or R$^6$ and an apolar solvent for causing substitution at R$^3$ or R$^4$.

2. A process for the preparation of a compound of the formula (I)

or a salt thereof wherein

R$^1$ and R$^2$ are each hydrogen or a C$_1$ to C$_4$ alkoxy group, or together form a methylenedioxy group;
one of R$^3$, R$^4$, R$^5$ and R$^6$ is beta-methoxycarbonylethyl, beta-cyanoethyl, beta-carboxyethyl, beta-aminocarbonylethyl, beta-chlorocarbonylethyl, beta-benzylaminocarbonylethyl, beta-morpholinocarbonyl-ethyl or beta-diethylaminocarbonyl-ethyl and each remaining moiety is a hydrogen which comprises the steps of
(a) reacting a compound of the formula (II)

with an organic secondary amine;
(b) reacting in a predetermined solvent the resulting enamine (III)

thus obtained, wherein R$^8$ and R$^9$ each represent a C$_1$ to C$_5$ alkyl group or together with the adjacent nitrogen atom form a 5- or 6-membered heterocyclic ring, with a compound of the formula:

$$CH_2=CH-(CH_2)_n-R^{10} \qquad (IV)$$

wherein R is a cyano group, carboxy or methoxycarbonyl;
(c) treating the reaction mixture of step (b) with water to yield the compound of Formula I or said salt thereof, wherein the position of substitution in step (b) is determined by the use of a polar protic solvent for causing substitution at R$^5$ or R$^6$ and an apolar solvent for causing substitution at R$^3$ or R$^4$; and (d) reacting the compound of Formula I wherein one of $R^3$, $R^4$, $R^5$ and $R^6$ is beta-methoxycarbonylethyl with ammonia to yield the compound of Formula I wherein one of $R^3$, $R^4$, $R^5$ and $R^6$ is beta-aminocarbonylethyl; reacting the compound of Formula I wherein one of $R^3$, $R^4$, $R^5$ and $R^6$ is beta-carboxyethyl with thionyl chloride to yield the compound of Formula I wherein one of $R^3$, $R^4$, $R^5$ and $R^6$ is beta-chlorocarbonylethyl; reacting the compound of Formula I wherein one of $R^3$, $R^4$, $R^5$ and $R^6$ is beta-chlorocarbonylethyl with benzylamine to yield the compound of Formula I wherein one of $R^3$, $R^4$, $R^5$ and $R^6$ is beta-benzylamino-carbonylethyl; reacting the compound of Formula I wherein one of $R^3$, $R^4$, $R^5$ and $R^6$ is beta-chlorocarbonylethyl with morpholine to yield the compound of Formula I wherein one of $R^3$, $R^4$, $R^5$ and $R^6$ is beta-morpholino-carbonylethyl; and reacting the compound of Formula I wherein one of $R^3$, $R^4$, $R^5$ and $R^6$ is beta-chlorocarbonylethyl with diethylamine to yield the compound of Formula I wherein one of $R^3$, $R^4$, $R^5$ and $R^6$ is beta-diethylamino-carbonylethyl.

3. The process defined in claim 2 wherein the polar protic solvent is methanol or ethanol.

* * * * *